United States Patent
Song et al.

(10) Patent No.: US 10,632,115 B2
(45) Date of Patent: Apr. 28, 2020

(54) USE OF A STATIN COMPOUND AS LOCAL DRUG FOR TREATING OBESITY, DIABETES, HYPERTENSION AND HYPERLIPEMIA

(71) Applicant: Peking University Third Hospital, Beijing (CN)

(72) Inventors: Chunli Song, Beijing (CN); Ning Yang, Beijing (CN); Yueyi Cui, Beijing (CN); Yingsheng Yu, Beijing (CN)

(73) Assignee: Peking University Third Hospital, Beijing (CN)

( * ) Notice: Subject to any disclaimer, the term of this patent is extended or adjusted under 35 U.S.C. 154(b) by 0 days.

(21) Appl. No.: 15/900,103

(22) Filed: Feb. 20, 2018

(65) Prior Publication Data
US 2018/0169093 A1 Jun. 21, 2018

Related U.S. Application Data

(62) Division of application No. 14/646,991, filed on May 22, 2015, now Pat. No. 9,895,366.

(51) Int. Cl.

| | | |
|---|---|---|
| *A61K 31/22* | (2006.01) | |
| *A61K 31/40* | (2006.01) | |
| *A61K 31/47* | (2006.01) | |
| *A61K 31/366* | (2006.01) | |
| *A61K 31/405* | (2006.01) | |
| *A61K 31/505* | (2006.01) | |
| *A61K 31/4418* | (2006.01) | |
| *A61K 9/00* | (2006.01) | |
| *A61K 9/08* | (2006.01) | |
| *A61K 47/10* | (2017.01) | |
| *A61K 9/107* | (2006.01) | |

(52) U.S. Cl.
CPC .......... *A61K 31/505* (2013.01); *A61K 9/0019* (2013.01); *A61K 9/08* (2013.01); *A61K 9/107* (2013.01); *A61K 31/22* (2013.01); *A61K 31/366* (2013.01); *A61K 31/40* (2013.01); *A61K 31/405* (2013.01); *A61K 31/4418* (2013.01); *A61K 31/47* (2013.01); *A61K 47/10* (2013.01)

(58) Field of Classification Search
CPC ........ A61K 31/22; A61K 31/40; A61K 31/47; A61K 31/366; A61K 31/405; A61K 31/505; A61K 31/4418; A61K 9/00; A61K 9/08
See application file for complete search history.

(56) References Cited

U.S. PATENT DOCUMENTS

2007/0003636 A1* 1/2007 Mach .................. A61K 31/192
424/649

OTHER PUBLICATIONS

Elsevier, Vaccine, vol. 20, issues 3-4, Nov. 12, 2001, pp. 532-537.*

* cited by examiner

*Primary Examiner* — Zohreh A Fay
(74) *Attorney, Agent, or Firm* — Fox Rothschild LLP

(57) ABSTRACT

The invention discloses a use of a statin compound in the preparation of local drugs for improving lipid metabolism and treating obesity, hypertension, hyperlipidemia, fatty liver and hyperglycemia; and statin compound local compositions for improving lipid metabolism and treating obesity, hypertension, fatty liver, hyperlipidemia, atherosclerosis, coronary heart disease, apoplexy and other cardiovascular and cerebrovascular diseases, and drug formulation and preparation method thereof.

3 Claims, 13 Drawing Sheets

USE OF A STATIN COMPOUND AS LOCAL DRUG FOR TREATING OBESITY, DIABETES, HYPERTENSION AND HYPERLIPEMIA

CROSS REFERENCE TO RELATED APPLICATION

This application is a Divisional of U.S. application Ser. No. 14/646,991, filed May 22, 2015, which is a U.S. National Phase application of International Application No. PCT/CN2013/001429 filed Nov. 22, 2013, which respectively claims priority to Chinese patent application 20120512630.8 filed Nov. 23, 2012 and Chinese patent application 201310426327.0 filed Sep. 18, 2013.

FIELD OF THE INVENTION

The present invention relates to medicine technology, and more specifically, it relates to a new use of HMG-CoA reductase inhibitor (statins compound) locally used for prevention and treatment of diabetes, obesity, hypertension, hyperlipidemia, artheroslerosis, cardiovascular and cerebrovascular diseases such as coronary heart diseases and stroke, fatty liver, and improving lipid metabolism; and to locally used composition.

BACKGROUND OF THE INVENTION

The prevalence and incidence of obesity is increasing dramatically either in developed or the developing country, and the age of patients suffering from obesity tended to be younger, it has been becoming a global epidemic of serious health effects. Obesity not only affect the daily life, induce psychological problem, and probably social discrimination; the most serious consequences is that obesity cause many diseases, such as type 2 diabetes, coronary heart diseases, hypertension, hyperlipidemia, cholecystitis, arthritis and some cancers, about 80% obesity combined one and 40% obesity combined two diseases mentioned above (Xu Manyin editor, diabetes, second edition, Shanghai science and technology publishing house).

Obesity may increase the burden of the tissues and organs, the most common diseases caused by obesity is fatty liver, hyperlipidemia, hypertension, coronary heart disease, type 2 diabetes, et al. The obesity is the prevention target of many diseases; body weight control is also for diabetes early prevention.

The risk of hypertension, hyperlipidemia is much higher in obese patients than those with normal body weight, and hypertension, hyperlipidemia is the important cause leading to arteriosclerosis, so the prevalence of coronary heart disease (CHD) is raised by obesity. As the excess energy intake are converted into fatty acids, the fatty acid is transported to the liver overmuch; the overdose fatty acid can't be digested by the liver cells, then cause fatty infiltration of liver cell, finally lead to fatty liver. Severe fatty liver can be turned into liver cirrhosis.

According to the report from the American National Association of Diabetes, in the light, moderate and severe obesity, the risk of development as type 2 diabetes, respectively is 2, 5, and 10 times of the normal body weight (Xu Manyin editor, diabetes, second edition, Shanghai science and technology publishing house).

The incidence of diabetes in the world has an increasing trend year by year, and diabetes has become the world's third chronic disease after tumor and cardio-cerebrovascular diseases, which cause serious damage to human health. In recent years the incidence of diabetes is higher and higher, the number of cases surged significantly. According to statistics, the morbidity in the population over 20 years old in China reached 9.7%, approaching 100 million people. The multiple system complications caused by diabetes have high mortality and morbidity, which cause serious damage to social health, result in high medical costs and heavy burden to the society. Diabetes mainly divided into two types, in type I diabetes (insulin dependent, IDDM), the insulin secretion is absolutely inadequate, exogenous insulin treatment is needed; in type II diabetes (non-insulin dependent, NIDDM), duo to the relative lack of insulin. NIDDM has the feature of fasting hyperglycemia and excessive postprandial plasma glucose levels. In NIDDM, high blood glucose, insulin resistance and insulin secretion deficiency leads to elevated blood glucose.

Diabetes treatments include insulin injected or inhaled, and oral medications; among them, oral medications include:

Sulfonylurea (e.g., tolbutamide, glyburide, glipizide, gliclazide, glimepiride and glipizide);

Glinides (e.g., repaglinide and nateglinide);

Biguanide (such as metformin and phenformin);

Insulin synergistic agent (such as rosiglitazone and pioglitazone);

Alpha glycosidase inhibitor (such as acarbose and voglibose).

In previous clinical studies, the effects of statins on diabetes is inconsistency (Swapnil N. Rajpathak et al., Statin therapy and risk of developing type 2 diabetes: a meta-analysis. Diabetes Care. 2009; 32(10): 1924-1929).

Tan et al. reported the effect of orally administrated atorvastatin on the blood glucose in type 2 diabetes. All the patients are treated with conventional antidiabetic, the experimental group is supplemented with atorvastatin 10 mg/d for 16 weeks, the results showed that the blood glucose in the atorvastatin group is much better than the control group.

Michiro, Ishikawa, et al. reported that in oral pravastatin and atorvastatin in non-diabetic patients with hypercholesterolemia trials found that oral pravastatin is good for glucose metabolism, and atorvastatin is opposite (DOI: 10.2169/internal medicine.45.1476). Jun Sasaki reviewed the impact of statins on diabetes mellitus and glucose metabolism, and describes that, orally administrated pravastatin is favourable on sugar metabolism, atorvastatin (10 mg/day) and simvastatin (40 mg/day) has no effect on diabetes. But orally administrated pravastatin and high dose atorvastatin (80 mg) is detrimental on glucose metabolism (Sasaki J1, Iwashita M, Kono S. Statins: beneficial or adverse for glucose metabolism. J Atheroscler Thromb. 2006 June; 13(3):123-9.).

But there are also large amount of clinical data showing that, taking statins increase the incidence of diabetes. Some clinical meta-analysis reported that statins would reduce cardiovascular events, but will slightly increase the risk of diabetes (Statins and risk of incident diabetes: a collaborative meta-analysis of randomised statin trials. Lancet. 2010; 375(9716): 735-742.), (Risk of incident diabetes with intensive-dose compared with moderate-dose statin therapy: a meta-analysis. JAMA. 2011; 305(24): 2556-2564.).

Hertension, hyperlipidemia, diabetes and obesity are all important cause of atherosclerosis, which caused great harm of cardiocerebrovascular events. So the lipid-lowering and antihypertensive treatment is important strategy to prevent cardiovascular events, respectively.

But without exception, these reports conclude that all are based on daily oral statins. Statins act as lipid-lowering, inhibiting the key enzyme (HMG-CoA reductase) used to lower cholesterol, are now in safe clinical application for decades, but it need daily use for a long-term.

SUMMARY OF THE INVENTION

The inventor was surprised to find that a local single application of statin compound (HMG CoA reductase inhibitors) can maintain a long time to promote the secretion of insulin, to increase insulin sensitivity of peripheral tissue, to lower blood glucose, and can be used in the treatment of diabetes.

The inventor also surprisingly found that a local single application of statin compound can maintain for a long time to reduce cholesterol, triglyceride and low density lipoprotein, to improve lipid metabolism; also, it can reduce body weight, reduce body fat, reduce fatty liver, and can be used in the treatment of obesity, hypertension, hyperlipidemia, fatty liver and improve lipid metabolism.

Intraosseous local single use of statin compounds can prevent cardiovascular and cerebrovascular events, and it can through the invention by local single intraosseous application of statin compound to prevent and cure atherosclerosis, coronary heart disease, stroke and other cardiovascular and cerebrovascular disease.

One purpose of the present invention is to provide a use of statin compounds (HMG CoA reductase inhibitors) as local single used drug for the prevention and treatment of diabetes, obesity, hypertension, hyperlipidemia, atherosclerosis, cardiovascular and cerebrovascular diseases such as coronary heart disease and stroke, fatty liver, or improving lipid metabolism.

Another purpose of the present invention is to provide the local pharmaceutical composition containing a statin compound for the prevention and treatment of diabetes, obesity, hypertension, hyperlipidemia, atherosclerosis, cardiovascular and cerebrovascular diseases such as coronary heart disease and stroke, fatty liver, or improving lipid metabolism, and its preparation method.

On one hand, the present invention provides a use of a statin compound (HMG CoA reductase inhibitor), or its pharmaceutically acceptable salt or a pharmaceutical composition containing a statin compound and/or its pharmaceutically acceptable salt in preparation of a medicament locally administered for prevention or treatment of non-insulin-dependent diabetes, obesity, hypertension, hyperlipidemia, atherosclerosis, cardiol cerebrol vascular diseases such as coronary heart disease and stroke, fatty liver or improving fat metabolism in mammals including human beings.

Specifically, the invention relates to a use of statin compounds (HMG CoA reductase inhibitors) in preparation of a medicament locally administered for the treatment of non insulin-dependent diabetes, obesity, high blood pressure, hyperlipoidemia, fatty liver or improving lipid metabolism; the invention also relates to a use of the statin compounds (HMG CoA reductase inhibitors) as a drug locally administered in the treatment of non insulin-dependent diabetes, obesity, high blood pressure, hyperlipoidemia, fatty liver or improve lipid metabolism; the invention also relates to a new method of local application of statin compounds (HMG CoA reductase inhibitors) for treatment of non insulin-dependent diabetes, obesity, high blood pressure, hyperlipoidemia, fatty liver or to improve lipid metabolism. This application also relates to a use of a pharmaceutical composition for preparation of a medicament locally administered for the treatment of non insulin-dependent diabetes in mammals, the pharmaceutical composition contain a statin compound or its pharmaceutically acceptable salt and a pharmaceutically acceptable carrier, diluent or excipient.

On the other hand, the present invention provides a pharmaceutical composition locally administered for prevention or treatment of non-insulin-dependent diabetes, obesity, hypertension, hyperlipidemia, atherosclerosis, cardiovascular and cerebrovascular diseases such as coronary heart disease and stroke, or fatty liver, or for improving fat metabolism, characterized in that it contain a statin compound or its pharmaceutically acceptable salt in a prophylactically or therapeutically effective amount and pharmaceutically acceptable carrier, diluent or excipient.

The drug is a non-storage form of local administration, preferably drug is a injectable dosage form administered skeletally, most preferably intraosseously. The amount of statin compound in the drug unit dosage form range from 0.1 mg to 1000 mg, preferably from 1 mg to 500 mg, more preferably from 2 mg to 200 mg, most preferably from 2 mg to 10 mg.

The statin compound of present invention comprise simvastatin, atorvastatin, fluvastatin, lovastatin, pravastatin, rosuvastatin, pitavastatin, bervastatin, cerivastatin, crilvastatin, dalvastatin, mevasatin or tenivastatin; preferably simvastatin, atorvastatin, fluvastatin, rosuvastatin; the most preferably simvastatin.

Said statin compounds also include pharmaceutically acceptable salt form, which may select from hydrochloride, hydrobromide, hydriodate, sulfate, nitrate, phosphate, citrate, mesylate, trifluoroacetate, acetate, or salt of sodium, potassium, magnesium, calcium, or magnesium thereof, such as atorvastatin calcium, sodium atorvastatin, sodium fluvastatin, sodium pravastatin, calcium rosuvastatin, or calcium pitavastatin.

The application also relates to a pharmaceutical composition, which contain a statin compound and a pharmaceutically acceptable carrier, diluent or excipient.

The application also relates to a pharmaceutical composition suitable for intraosseous injection, which contain a statin compound and a pharmaceutically acceptable carrier, diluent or excipient.

This application also relates to a pharmaceutical formulation locally administered for the prevention or treatment of non-insulin-dependent diabetes, obesity, hypertension, Hyperlipidemia, atherosclerosis, cardiovascular and cerebrovascular disease such as coronary heart disease and stroke, or fatty liver, or for improving lipid metabolism, characterized in that it contains an effective amount of statin compounds and pharmaceutically acceptable carriers, diluents or excipients. By effective amount meant an amount that after local administration, the formulation can be effective in preventing or treating diabetes, obesity, hypertension, hyperlipidemia, fatty liver, atherosclerosis, cardiovascular and cerebrovascular diseases such as coronary heart disease and stroke. Preferably, the formulation is an injectable dosage form suitable for intraosseous administration.

This application also involves a method of preparing a pharmaceutical composition, comprise a procedure of mixing a statin compound in a therapeutically effective amount with a pharmaceutically acceptable carrier, diluent or excipient; for example, dissolving or suspending the statin compound in a therapeutically effective amount in said pharmaceutically acceptable carrier, diluent or excipient.

This application also involves a method of preparing a pharmaceutical formulation, characterized by mixing a statin compound in a therapeutically effective amount with a pharmaceutically acceptable carrier, diluent or excipient to form a pharmaceutical formulation locally administered; preferably, to form an injectable dosage form suitable for intraosseous administration.

In a specific embodiment of the present invention, the local statin drugs (or composition) is administered preferably via injection into bone, and the local statin drugs described in present invention can exist in the form of injectable dosage forms. The injectable dosage forms include, but not limited to, the injectable solution, injectable suspension liquid, injectable emulsion, injectable gel, injectable solid form, or their slow or controlled release form. Here, the injectable solid form refers to those that is mixed with a solvent such as water for injection, normal saline injection or glucose solution for injection when it is used, to make it feasible for intraosseous injection.

In some specific embodiment of the present invention, the local statin drugs (or composition) comprise a statin compound or its pharmaceutically acceptable salt and pharmaceutically acceptable carrier, diluent or excipient. Here, said pharmaceutical acceptable carrier, diluent or excipient can be selected from at least one of the optional water-soluble solvent or oily solvent, dispersing agent, isotonic agent, preservative, solubilizer or stabilizers; water-soluble solvent can be selected from distilled water, normal saline, Ringer's solution or phosphate buffer (PBS); oil soluble solvent can be selected from vegetable oil, such as olive oil, castor oil, sesame oil, cottonseed oil or corn oil; dispersing agent can be selected from tween 20 or tween 80, polyethylene glycol, carboxy methyl cellulose, and/or sodium alginate; isotonic agent can be selected from chloride sodium, glycerol, sorbic alcohol, or glucose; Solubilizer can be selected from salicylic acid sodium, poloxamer or acetate sodium; preservative may be selected from methyl paraben, propyl paraben, benzyl alcohol, chlorobutanol, sodium benzoate, or phenol; stabilizer may be selected from albumin, such as human serum albumin, bovine serum albumin, etc; preferably, said pharmaceutically acceptable carrier, diluents or excipients can also be selected from biodegradable materials, such as polylactide, poly-1-lactide-glycolide, polyaspartic acid, and so on.

For a person skilled in the art, the statin local medicament (or composition) of the present invention can be prepared through known preparation technology. For example, the statin compound or its pharmaceutically acceptable salt together with dispersing agent, and/or isotonic agent, and/or preservative, and/or solubilizer and/or stabilizers are dissolved, suspended or emulsified in water-soluble solvent or oil-soluble solvent (Remington: the science and practice of pharmacy, 21st edition, 2005, Lippincott Williams, is incorporated into text by reference).

In the invention, the dosing interval of the administration of the statin local composition to mammalian is once every 7 days up to 600 days, preferably 10 to 500 days at a time, more preferably 20 to 400 days at a time, most preferably 30 to 300 days at a time. In terms of the administration of the statin local composition to mammalian, a single dose of statin compound is from 0.1 mg to 1000 mg, preferably from 1 mg to 500 mg, more preferably from 2 mg to 200 mg. A clinician can adjust or modify the frequency and dose of administration according to needs of the clinical effect under the guidance of the present invention.

In a specific embodiment of the present invention, the invention provides a local compositions for the treatment of diabetes, wherein a statin compound or its pharmaceutically acceptable salts is present in a pharmacologically effective amount from 0.1 mg to 1000 mg, preferably from 1 mg to 500 mg, more preferably from 2 mg to 200 mg, most preferably from 2 mg to 10 mg. In addition, the dosing interval of the administration of the statin local composition to mammalian is once every 7 days up to 600 days, preferably 10 to 500 days at a time, more preferably 20 to 400 days, most preferably 30 to 300 days at a time. A person skilled in the art can adjust or modify the frequency and dosage of local administration based on the clinical therapeutic effect requirement.

In a specific embodiment of the present invention, the local statin drugs (or composition) is administered preferably via injection into bone or embedding in bone. Here, the bones can be chosen from, but not limited to, ilium, radius distal, phalanx, tibia, vertebral body or any other bone which is convenient for local drug delivery; preferably bones with the bone marrow cavity therein.

In an embodiment of the invention, preferably a mammal is human being.

Experiments show that, single, local administration of statin composition of the invention at bone containing a bone marrow cavity can significantly induce serum insulin levels, increase insulin sensitivity, and obviously reduce the blood glucose of diabetic mammals. More importantly, a single injection can keep a long curative effect, avoid the currently daily diabetes treatment such as everyday oral administration or subcutaneous insulin injection, enhance therapeutic compliance and convenience. Most importantly, a single local injection promote the endogenous insulin secretion and enhance the insulin sensitivity. It is much better than the existing treatment for diabetes.

Experiments also show that, the single intraosseous administration of the statin compound of the present invention can significantly reduce low-density lipoprotein (LDL), cholesterol, triglyceride and obviously reduce weight, reduce body fat, reduce fatty liver; and a single injection can keep a long curative effect, avoid the currently daily treatment of obesity and lipid metabolism which need administration every day. The invention can enhance therapeutic compliance and convenience. These effects are independent of liver HMG CoA reductase, showing better therapeutic effect, longer lasting effect but lower doses required.

DESCRIPTION OF THE PREFERRED EMBODIMENTS

Figure 1:
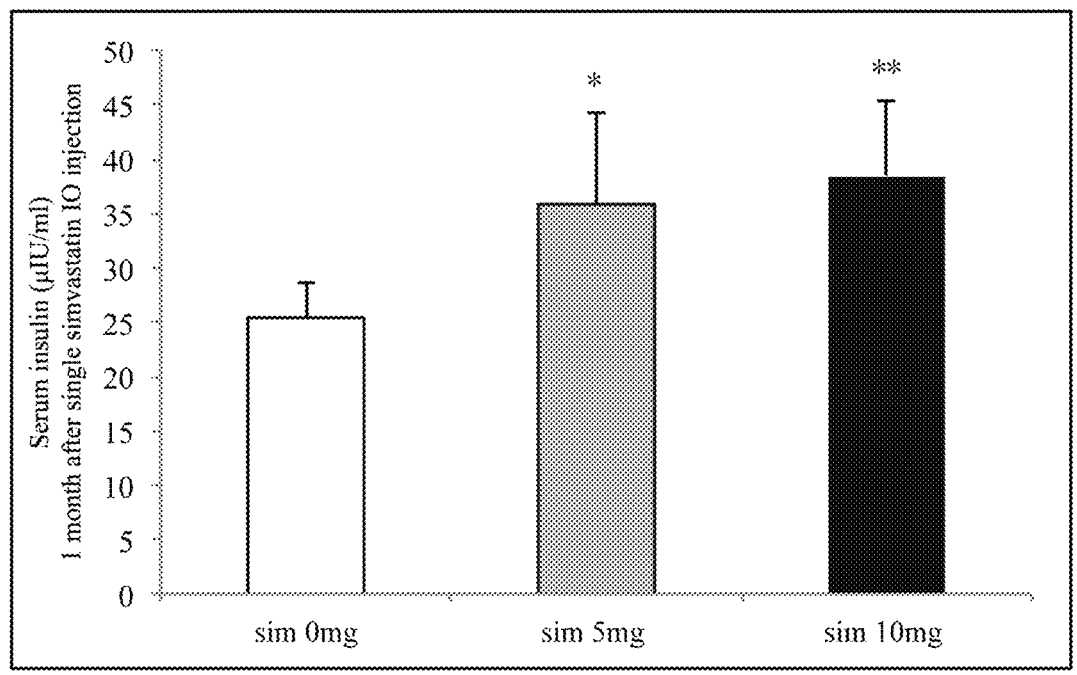
FIG. 1 shows the changes of serum insulin levels one month after a local, single injection of simvastatin into femoral marrow cavity in ovariectomized rats. After 3 months of ovariectomized, simvastatin (0, 5, 10 mg) (formula of example 1 of the present invention) was injected in the right femoral medullary cavity of the ovariectomized rats, 1 month later, the rats were euthanasized by excessive anesthesia, serum were collected, serum insulin level were detected. Results show that the serum insulin level is significantly increased (*<0.05 and **p<0.01, compared with the control group).

The present invention are described in detail using examples given below, but in any case the examples shall not be construed as a restriction to the scope of the present invention.

The Preparation of Pharmaceutical Composition

Example 1

Preparation of Local Injection of Simvastatin

Simvastatin 1000 mg was dissolved in PBS phosphate buffer 10 ml (Beijing Zhongshan Golden Bridge Biotechnology Co., Ltd.), PBS solution containing 2% DMSO (Dimethyl Sulfoxide, DMSO, purchased from Sigma) and 0.1% bovine serum albumin (Bovine Serum Albumin, BSA, purchased from Sigma), and the resulting solution was made homogeneous, then got a composition.

Example 2

Preparation of Local Injection of Provastatin

Pravastatin sodium 1000 mg was suspended in lipid emulsion (Intralipid) 10 ml and the resulting solution is homogenized.

Example 3

Preparation of Local Injection of Fluvastatin

The fluvastatin sodium 1000 mg was dissolved in 10 ml physiological saline containing 3% Poloxamer 188 (Germany BSF Company), homogeneous solution was obtained.

Example 4

Preparation of Local Injection of Atovastatin

The atorvastatin calcium 1000 mg was dissolved in PBS phosphate buffer 10 ml (Beijing Zhongshan Golden Bridge Biotechnology Co., Ltd.), PBS solution containing 2% DMSO (Dimethyl Sulfoxide, DMSO, purchased from Sigma) and 0.1% bovine serum albumin (Bovine Serum Albumin, BSA, purchased from Sigma), and the resulting solution is homogeneous that is convenient for injection.

Example 5

Preparation of Local Injection of Rosuvastatin

The rosuvastatin calcium 1000 mg was dissolved in 10 ml physiological saline containing 3% Poloxamer 188 (Germany BSF Company), homogeneous solution was obtained.

Example 6

Preparation of Local Injection of Simvastatin simvastatin sodium 1000 mg was suspended in lipid emulsion (Intralipid) 10 ml and the resulting solution was homogenized.

Example 7

Preparation of Local Injection of Tenivastatin

The tenivastatin 8000 mg was dissolved in PBS phosphate buffer 10 ml (Beijing Zhongshan Golden Bridge Biotechnology Co., Ltd.), PBS solution containing 2% DMSO (Dimethyl Sulfoxide, DMSO, purchased from Sigma) and 0.1% bovine serum albumin (Bovine Serum Albumin, BSA, purchased from Sigma), and the resulting solution is homogeneous that is convenient for injection.

Example 8

Preparation of Local Injection of Pitavastatin

The pitavastatin 200 mg was dissolved in 10 ml physiological saline containing 3% Poloxamer 188 (Germany BSF Company), homogeneous solution was obtained.

Diabetes Pharmacological Experiment of Pharmaceutical Preparations

The Experimental Example 1

A Single Dose of Simvastatin Intraosseous Injection Promotes Insulin Secretion in Ovariectomized Rats In accordance with standard operating procedures, adult female rats were bilateral ovariectomized. In short, three month old female SD rats (weighing 200-250 g) were anesthesiaed (10% chloral hydrate intraperitoneal injection of anesthesia, 3 ml/kg), the left and right sides of the back of the rats were incised and carefully find the ovaries in the fat tissue, the both ovaries were removed. After 3 months, the rats were randomly divided into three groups (control, simvastatin 5 mg, simvastatin 10 mg), n=12 for each group, under anesthesia (10% chloral hydrate intraperitoneal injection, 3 ml/kg) and sterile condition, incised 0.5 cm under the right side of the greater trochanter, in the lateral of femurs, a medullo-puncture needle (diameter 1 mm) penetrate the cortical bone, simvastatin injection prepared according to Example 1 method, containing simvastatin 5 mg, simvastatin 10 mg or only vehicle (PBS buffer, 0.1% BSA, 2% DMSO) respectively, were injected with micro syringe. Bone wax pinhole puncture closure avoiding leakage and sutured wounds.

Figure 2:
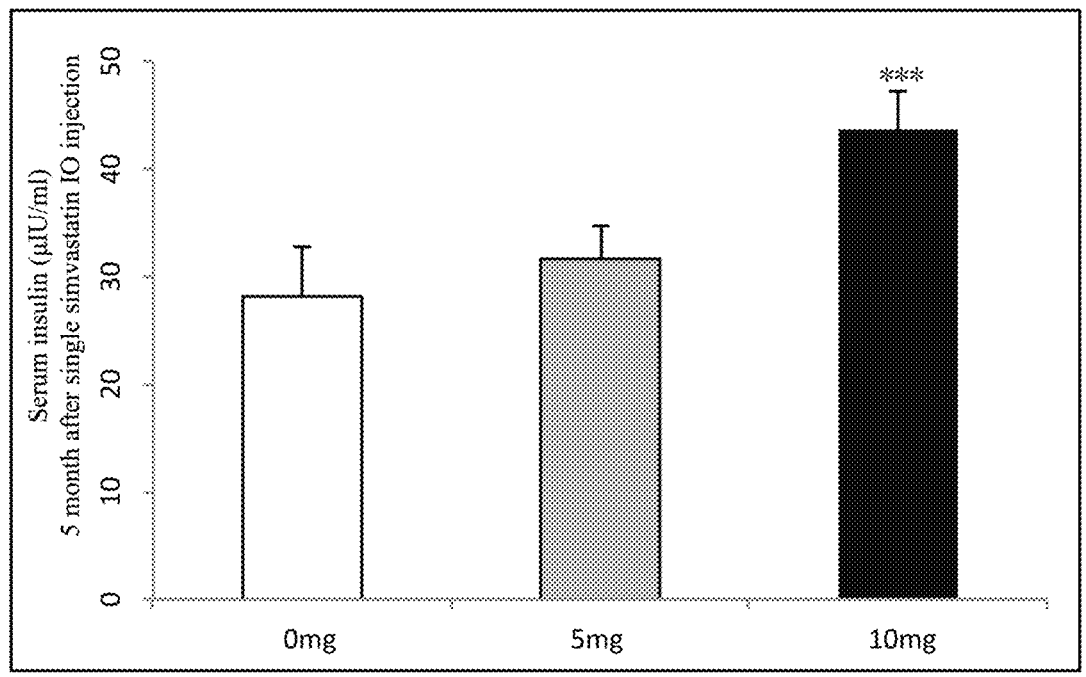
FIG. 2 shows the changes of serum insulin levels five month after a local, single injection of simvastatin into femoral marrow cavity in ovariectomized rats. After 3 months of ovariectomized, simvastatin (0, 5, 10 mg) (formula of example 1 of the present invention) was injected in the right femoral medullary cavity of the ovariectomized rats, 5 month later, the rats were euthanasized by excessive anesthesia, serum were collected, serum insulin level were detected. Results show that the serum insulin level is significantly increased (**p<0.01, compared with the control group).

One and five months later respectively, randomly selected six from each group, the rats were euthanasized by overdose anesthesia, collect serum, I-125 labeled radioimmunoassay (I-125 labeled radioimmunoassay kit purchased from Beijing North biotechnology Institute) with BH6020 type modular counter (Beijing nuclear Instrument Factory) was measured insulin levels. Surprisingly, serum insulin levels were significantly increased in a dose-dependent manner in the intraosseous injected with simvastatin, a single intraosseous injection of simvastatin significantly increased insulin levels and promote sustainable at least five months. (FIG. 1—insulin levels one month after local injection) (FIG. 2—insulin levels five month after local injection).

The Experimental Example 2

Diabetes Mellitus Rat Model of Intraosseous Injection of Simvastatin 36 three-month-old male SD rats (250-300 g) rats were accommodated for one week, in accordance with standard procedures of diabetic rat model, intraperitoneal injection of streptozotocin (STZ, Sigma Company) 40 mg/kg, the next day administration of high fat diet (purchased from Institute of Zoology, recipe: 68.5% base stock, lard 20%, 10% sucrose, 1% cholesterol and 0.5% porcine bile salts).

Two months later, all the rats were abnormally elevated blood glucose (above 19.5 mmol/L), indicate a successful model (Zhouguang Xing animal models of human disease replication methodology Shanghai Science and Technology Literature Press, 2008: 167-168 SHI Xin animal models of human disease People's Health Press, 2008: 301-305). After the diabetic model is to be established, the experimental animals were randomly divided into three groups (control group, simvastatin 5 mg group, simvastatin 10 mg group), n=12 for each group. The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, simvastatin injection prepared according to Example 1 method, containing simvastatin 5 mg, simvastatin 10 mg or only vehicle (PBS buffer, 0.1% BSA, 2% DMSO) respectively, were injected with micro syringe. Bone wax pinhole puncture closure avoiding leakage and sutured wounds.

The Experimental Example 3

Fasting Blood Glucose Assay

Figure 3:
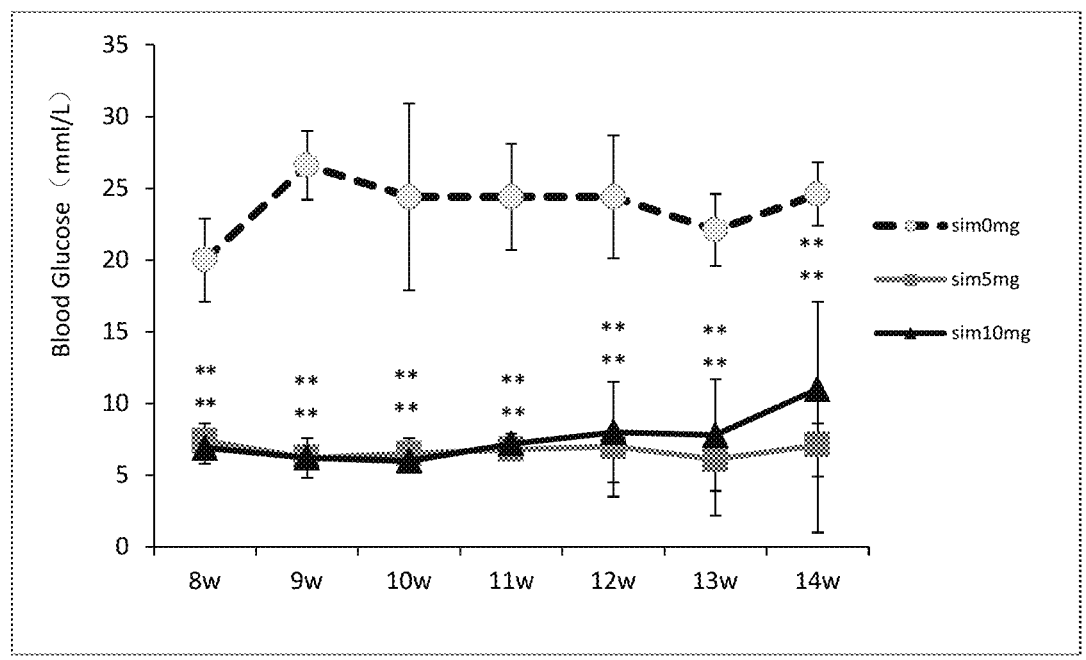
FIG. 3 shows the fasting blood glucose changes 8-14 weeks after a local, single injection of simvastatin into femoral marrow cavity in diabetic rats. The fasting blood glucose were detected 8 weeks to 14 weeks after single intraosseous injection of simvastatin (see formula of example 1) into the diabetic rats femoral marrow cavity, respectively. At the same time point, blood were collected via rat tail after 12 h of fasting, glucose meter measuring blood glucose change. The results show that a single local intraosseous injection of simvastatin significantly reduced fasting blood glucose, and this effect sustained at least 14 weeks.

The fasting rats blood glucose were detected weekly, 8 weeks after local single intraosseous injection of simvastatin by means of femoral medullary cavity. After the rats were fasted 6 h, take one drop of blood (about 50 ul) from the rat tail and placed in the blood sugar test paper (Roche), 2 seconds later, fasting blood glucose were determinated by Roche glucose meter (ACCU-CHEK Performa). Results show that blood glucose was significantly reduced after a single local intraosseous injection of simvastatin by means of femoral medullary cavity, at least continuing to 14 weeks (FIG. 3).

Figure 4:
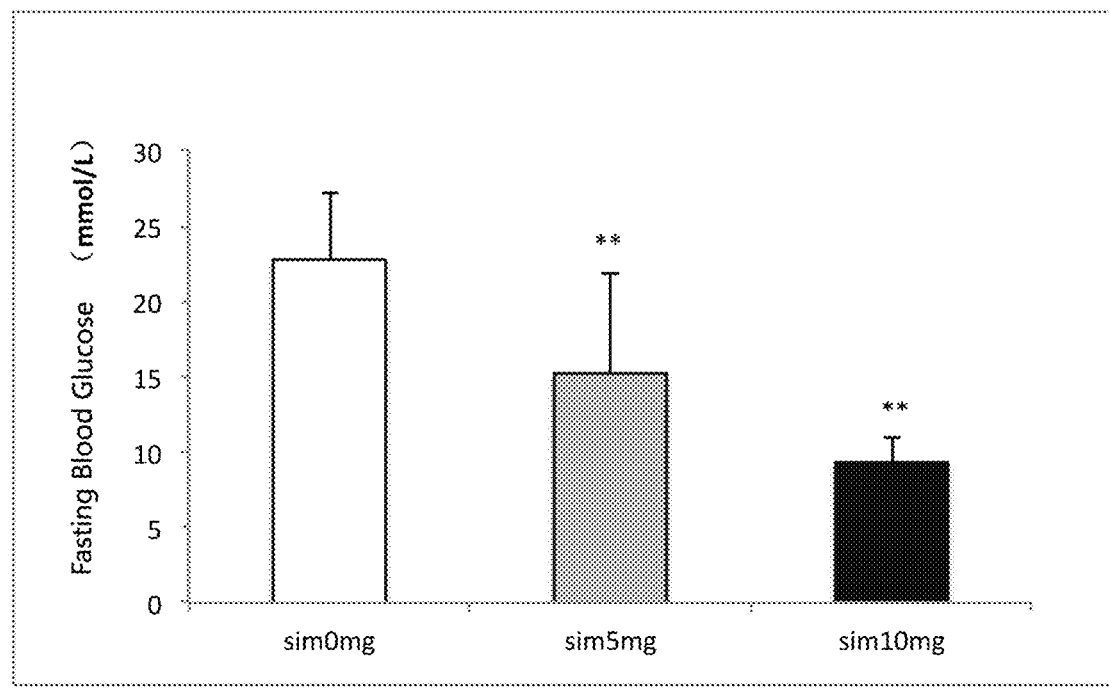
FIG. 4 shows the fasting blood glucose changes 15 weeks after a local, single injection of simvastatin into femoral marrow cavity in diabetic rats. The fasting blood glucose were detected 15 weeks after single intraosseous injection of simvastatin (see formula of example 1) into the diabetic rats femoral marrow cavity. At the same time point, blood were collected via abdominal aorta after 8 h of fasting, glucose meter measuring blood glucose change. The results single local intraosseous injection of simvastatin significantly reduced fasting blood glucose, and this effect sustained at least 15 weeks.

The rats were killed to take blood, blood glucose levels were measured using blood biochemical Analyzer, results showed that blood glucose was significantly decreased (FIG. 4).

The Experimental Example 4

Glucose Tolerance Test (GTT)

Figure 5:
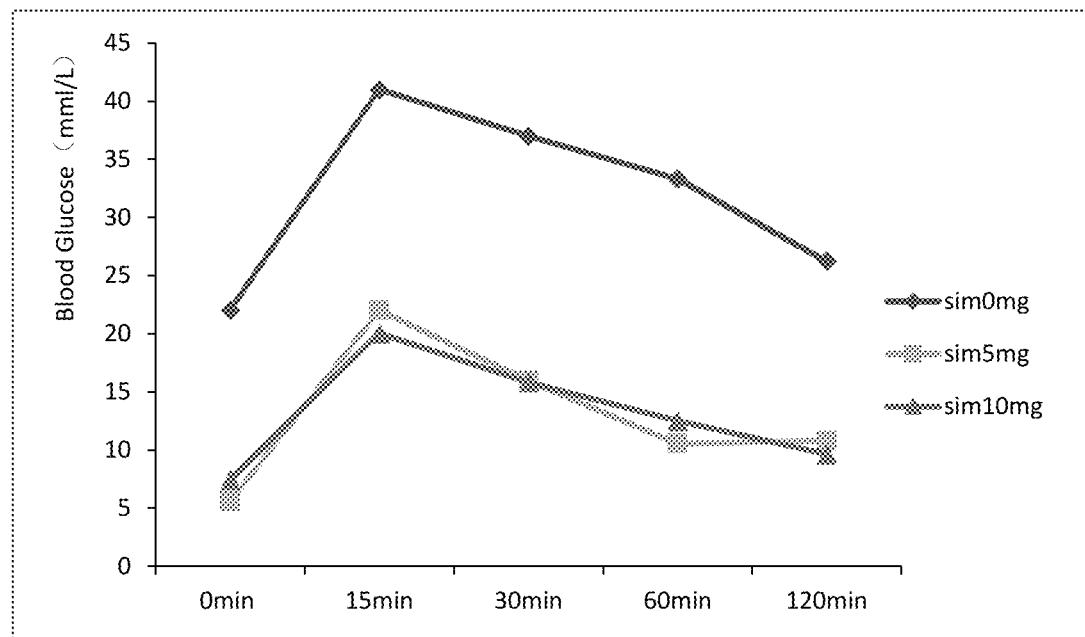
FIG. 5 shows the result of glucose tolerance test (GTT) 11 weeks after a local, single injection of simvastatin (see formula of example 1) into femoral marrow cavity in diabetic rats. According to the standard protocol, fasting in rats after 12 h, intraperitoneal injection of glucose (2 g/kg), GTT test were conducted by blood glucose meter.

To further verify anti-diabetic therapeutic effect of single local intraosseous injection of simvastatin by means of femoral medullary cavity, we conducted intraperitoneal injection of glucose tolerance tests. 11 weeks after intraosseous injection of simvastatin, the rats were overnight fasting for 12 h. After intraperitoneal injection of glucose (2 g/kg, China otsuka pharmaceutical co., LTD), and collecting blood from tail vein 0, 15, 30, 60, 120 minutes respectively, the blood glucose were assayed with blood glucose meter (ACCU-CHEK Performa) blood glucose (Mauvais-Jarvis F, Ueki K, Fruman D A, et al. Reduced expression of the murine p85alpha subunit of phosphoinositide 3-kinase improves insulin signaling and ameliorates diabetes. J Clin Invest. 2002; 109(1): 141-149) (Results were show in FIG. 5).

The Experimental Example 5

Insulin Tolerance Test (ITT)

Figure 6:
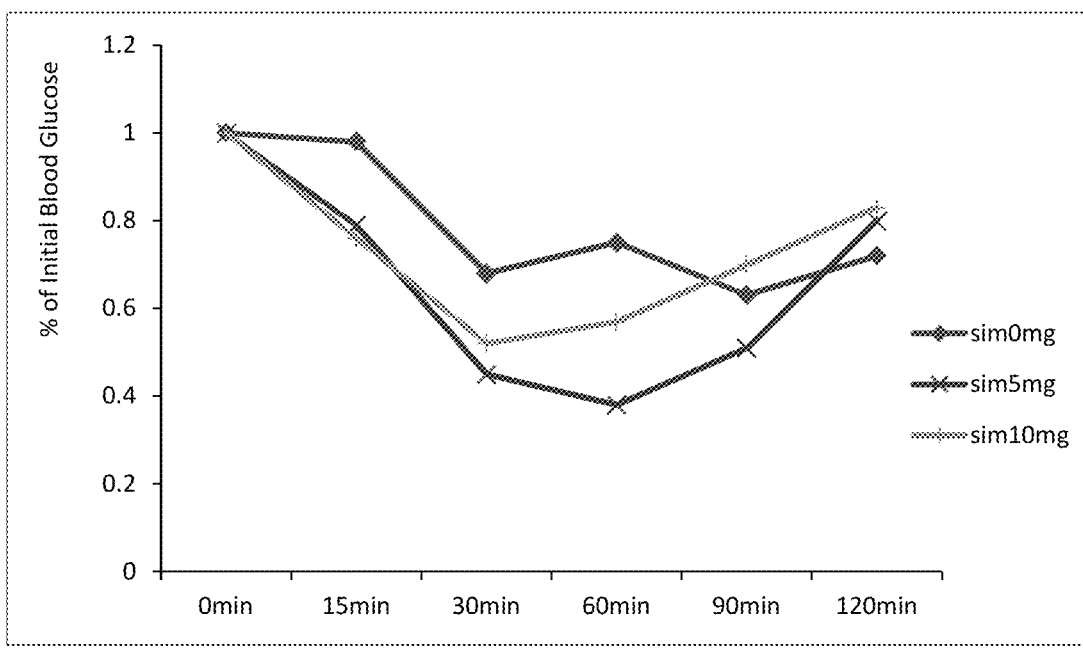
FIG. 6 shows the result of insulin tolerance test (ITT) 11 weeks after a local, single injection of simvastatin (see formula of example 1) into femoral marrow cavity in diabetic rats. According to the standard protocol, fasting in rats after 12 h, intraperitoneal injection of neutral insulin (1 U/kg), ITT test were conducted by blood glucose meter.

To further verify anti-diabetic therapeutic effect of single local intraosseous injection of simvastatin by means of femoral medullary cavity, we conducted the insulin tolerance test. 11 weeks after intraosseous injection of simvastatin, rats were fasted for 6 h and intraperitoneal injection neutral insulin (1 U/kg, Wanbang pharmacy), collected blood in the tail vein 0, 15, 30, 60, 90, 120 minute later respectively, in the light of reported methods (Mauvais-Jarvis f, Ueki k, Fruman D A, et al. Reduced expression of the murine p85alpha subunit of phosphoinositide 3-kinase improves insulin signaling and ameliorates diabetes. J Clin Invest. 2002; 109:141-149.), blood glucose were assayed with Roche blood glucose meter (ACCU-CHEK Performa), and calculate the ratio of initial blood glucose. Results show that single local intraosseous injection of simvastatin by means of femoral medullary cavity could significantly improve insulin sensitivity (results shown in FIG. 6.)

The Experimental Example 6

Glucose-Stimulated Insulin Secretion Test (GSIS)

Figure 7:
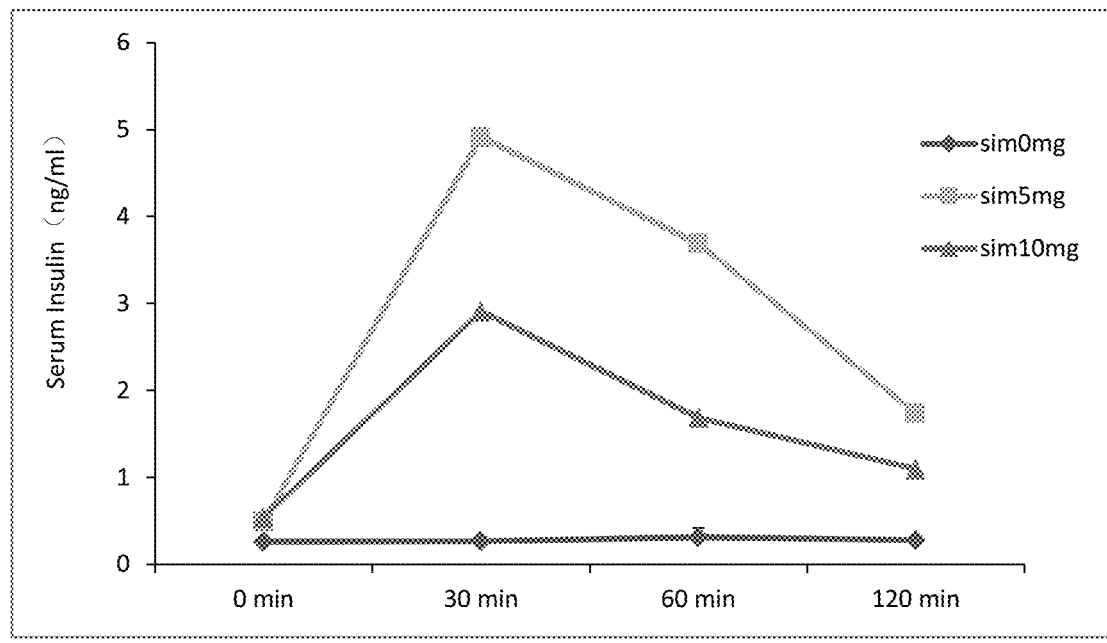
FIG. 7 shows the result of glucose-stimulated insulin secretion (GSIS) 14 weeks after a local, single injection of simvastatin (see formula of example 1) into femoral marrow cavity in diabetic rats. According to the standard protocol, after fasting for 12 h, rats with intraperitoneal injection of glucose (3 g/kg, China otsuka pharmaceutical co., LTD), gathering blood from tail vein of rats, the insulin level were detected with trace determination of insulin assay Kit.

To further verify anti-diabetic therapeutic effect of single local intraosseous injection of simvastatin by means of femoral medullary cavity, we conducted the glucose-stimulated insulin secretion test. After 14 weeks of single local intraosseous injection of simvastatin, the rats were fasted 12 h, intraperitoneal injections of glucose in rats (3 g/kg, China otsuka pharmaceutical co., LTD.), and respectively in 0, 30, 60, 120 minutes collecting vein blood of rats tail, the blood was collected from the rats tail in all 200 ul, let stand at room temperature for 5 minutes, centrifugal 4000 rpm for 10 minutes, take about 20 ul, serum rat trace insulin were detected with serum rat trace insulin assay kit (Millipore Corp., Billerica, Mass. company) on the microplate reader (Thermo Fisher Scientific). Results were shown in FIG. 7).

The Experimental Example 7

Diabetes Mellitus Rat Model of Intraosseous Injection of Fluvastatin 36 three-month-old male SD rats (250-300 g) were accommodated for one week, in accordance with standard procedures of diabetic rat model, intraperitoneal injection of streptozotocin (STZ, Sigma Company) 40 mg/kg, the next day administration of high fat diet (purchased from Institute of Zoology, recipe: 68.5% base stock, lard 20%, 10% sucrose, 1% cholesterol and 0.5% porcine bile salts).

Two months later, all the rats were abnormally elevated blood glucose (above 19.5 mmol/L), indicate a successful model (Zhouguang Xing animal models of human disease replication methodology Shanghai Science and Technology Literature Press, 2008: 167-168 SHI Xin animal models of human disease People's Health Press, 2008: 301-305). After the diabetic model is to be established, the experimental animals were randomly divided into two groups (vehicle and fluvastatin 8 mg), n=12 for each group. The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, fluvastatin injection prepared according to Example 3 method, containing fluvastatin 8 mg or only vehicle (3% poloxamer 188 normal saline) respectively, were injected with micro syringe. Bone wax pinhole puncture closure avoiding leakage and sutured wounds.

Fasting Blood Glucose Assay

Figure 8:
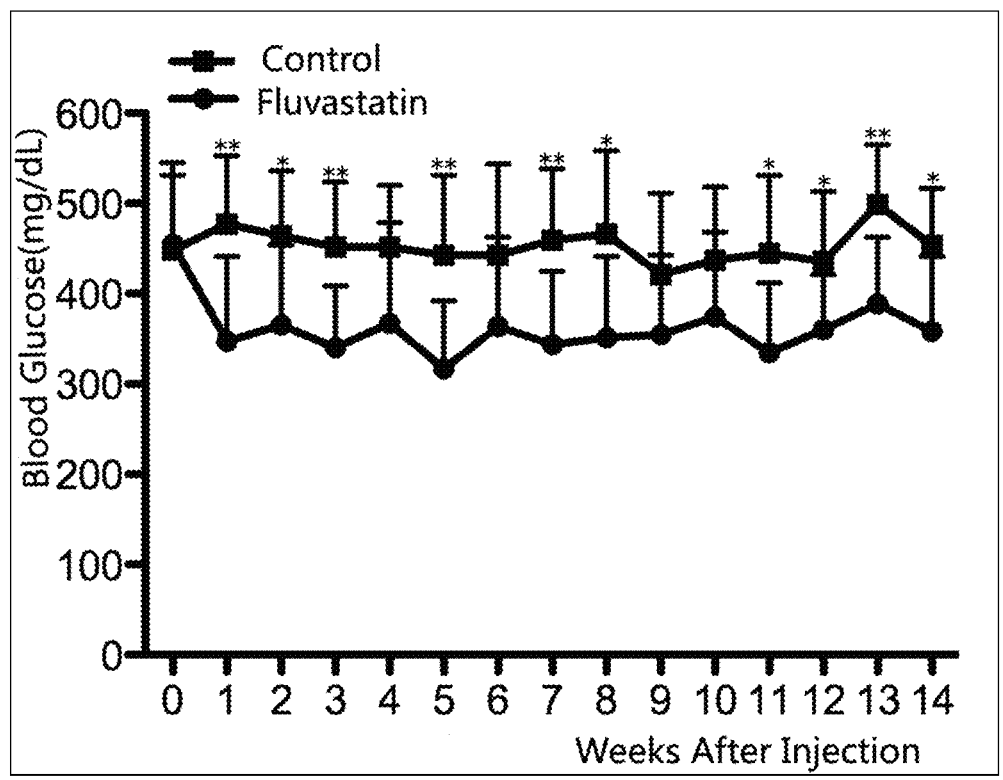
FIG. 8 shows the fasting blood glucose changes 1-14 weeks after a local, single injection of fluvastatin (see formula of example 3) into femoral marrow cavity in diabetic rats. The fasting blood glucose were detected 1 weeks to 14 weeks after single intraosseous injection of fluvastatin into the diabetic rats femoral marrow cavity, respectively. At the same time point, blood were collected via rat tail after 12 h of fasting, glucose meter measuring blood glucose changes. The results show that a single local intraosseous injection of fluvastatin significantly reduced fasting blood glucose, and this effect sustained at least 14 weeks.

The fasting rats blood glucose were detected weekly, 1 weeks after local single intraosseous injection of fluvastatin by means of femoral medullary cavity. After the rats were fasted 6 h, take one drop of blood (about 50 ul) from the rat tail and placed in the blood sugar test paper (Roche), 2 seconds later, fasting blood glucose were determined by Roche glucose meter (ACCU-CHEK Performa). Results show that blood glucose significantly reduced after a single local intraosseous injection of fluvastatin, at least continuing to 14 weeks (FIG. 8).

The Experimental Example 8

Diabetes Mellitus Rat Model of Intraosseous Injection of Atorvastatin by Means of Femoral Medullary Cavity Thirty six 3-month-old male SD rats (250-300 g) were accommodated for one week, in accordance with standard procedures of diabetic rat model, intraperitoneal injection of streptozotocin (STZ, Sigma Company) 40 mg/kg, the next day administration of high fat diet (purchased from Institute of Zoology, recipe: 68.5% base stock, lard 20%, 10% sucrose, 1% cholesterol and 0.5% porcine bile salts).

Two months later, all the rats were abnormally elevated blood glucose (above 19.5 mmol/L), indicate a successful model (Zhouguang Xing. Animal models of human disease replication methodology Shanghai Science and Technology Literature Press, 2008: 167-168 SHI Xin animal models of human disease People's Health Press, 2008: 301-305). After the diabetic model is to be established, the experimental animals were randomly divided into two groups (vehicle and atorvastatin 4 mg), n=12 for each group. The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, atorvastatin injection prepared according to Example 4 method, containing atorvastatin 4 mg or only vehicle (3% poloxamer 188 normal saline) respectively, were injected with micro-syringe. Bone wax pinhole puncture closure avoiding leakage and sutured wounds.

Fasting Blood Glucose Assay

Figure 9:
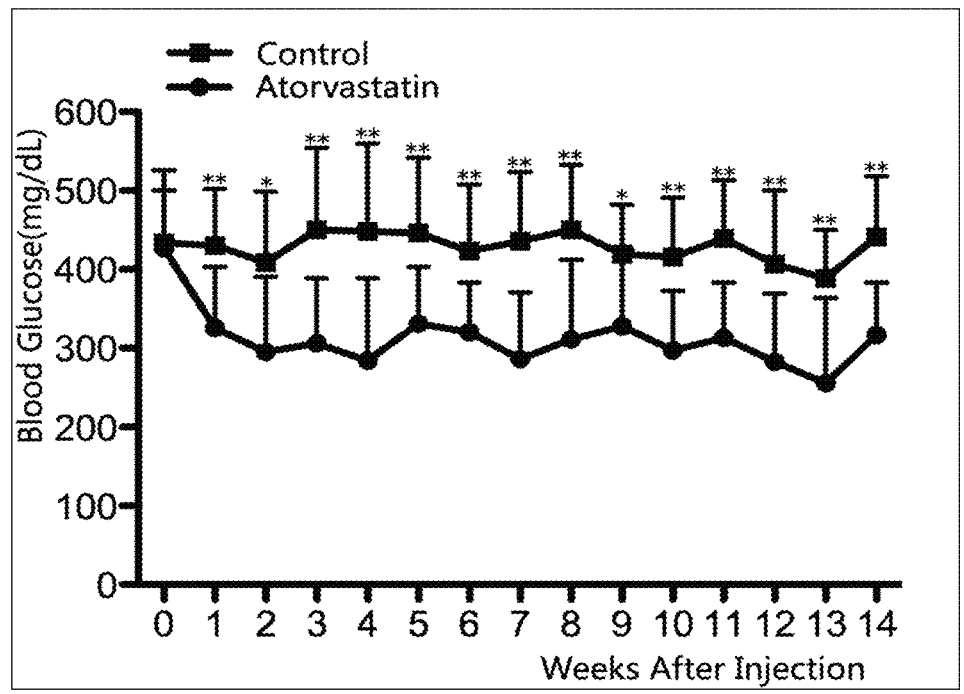
FIG. 9 shows the fasting blood glucose changes 1-14 weeks after a local, single injection of atorvastatin (see formula of example 4) into femoral marrow cavity in diabetic rats. The fasting blood glucose were detected 1 weeks to 14 weeks after single intraosseous injection of atorvastatin into the diabetic rats femoral marrow cavity, respectively. At the same time point, blood were collected via rat tail after 12 h of fasting, glucose meter measuring blood glucose changes. The results show that a single local intraosseous injection of atorvastatin significantly reduced fasting blood glucose, and this effect sustained at least 14 weeks.

The fasting glucose were detected weekly, 1 weeks after local single intraosseous injection of atorvastatin by means of femoral medullary cavity. After the rats were fasted 6 h, take one drop of blood (about 50 ul) from the rat tail and placed in the blood sugar test paper (Roche), 2 seconds later, fasting blood glucose were determined by Roche glucose meter (ACCU-CHEK Performa). Results show that blood glucose significantly reduced after a single local intraosseous injection of atorvastatin by means of femoral medullary cavity, at least continuing to 14 weeks (FIG. 9).

The Experimental Example 9

Glucose Tolerance Test (GTT)

Figure 10:
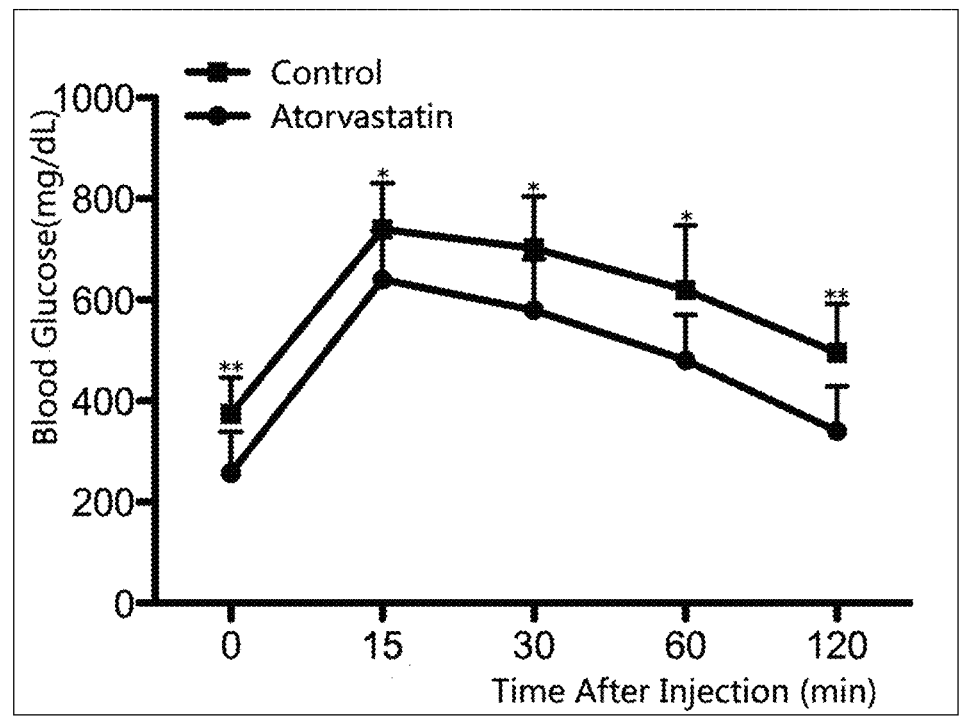
FIG. 10 shows the result of glucose tolerance test (GTT) 11 weeks after a local, single injection of atorvastatin (see formula of example 4) into femoral marrow cavity in diabetic rats. According to the standard protocol, fasting in rats after 12 h, intraperitoneal injection of glucose (2 g/kg), GTT test were conducted by blood glucose meter.

To further verify anti-diabetic therapeutic effect of single local intraosseous injection of atorvastatin by means of femoral medullary cavity, we conducted intraperitoneal injection of glucose tolerance tests. 11 weeks after intraosseous injection of atorvastatin, the rats were overnight fasting for 12 h. After intraperitoneal injection of glucose (2 g/kg, China otsuka pharmaceutical co., LTD), and collecting blood from tail vein 0, 15, 30, 60, 120 minutes respectively, the blood glucose were assayed with blood glucose meter (ACCU-CHEK Performa) blood glucose (Mauvais-Jarvis F, Ueki K, Fruman D A, et al. Reduced expression of the murine p85alpha subunit of phosphoinositide 3-kinase improves insulin signaling and ameliorates diabetes. J Clin Invest. 2002; 109(1): 141-149). Results were shown in FIG. 10.

The Experimental Example 10

Diabetes Mellitus Rat Model of Intraosseous Injection of Rosuvastatin by Means of Femoral Medullary Cavity Thirty-six 3-month-old male SD rats (250-300 g) were accommodated for one week, in accordance with standard procedures of diabetic rat model, intraperitoneal injection of streptozotocin (STZ, Sigma Company) 40 mg/kg, the next day administration of high fat diet (purchased from Institute of Zoology, recipe: 68.5% base stock, lard 20%, 10% sucrose, 1% cholesterol and 0.5% porcine bile salts).

Two months later, all the rats were abnormally elevated blood glucose (above 19.5 mmol/L), indicate a successful model (Zhouguang Xing. Animal models of human disease replication methodology Shanghai Science and Technology Literature Press, 2008: 167-168 SHI Xin animal models of human disease People's Health Press, 2008: 301-305). After the diabetic model is to be established, the experimental animals were randomly divided into two groups (vehicle and rosuvastatin 2 mg), n=12 for each group. The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, rosuvastatin injection prepared according to Example 5 method, containing rosuvastatin 2 mg or only vehicle (3% poloxamer 188 normal saline) respectively, were injected with micro-syringe. Bone wax pinhole puncture closure avoiding leakage and sutured wounds.

Fasting Blood Glucose Assay

Figure 11:
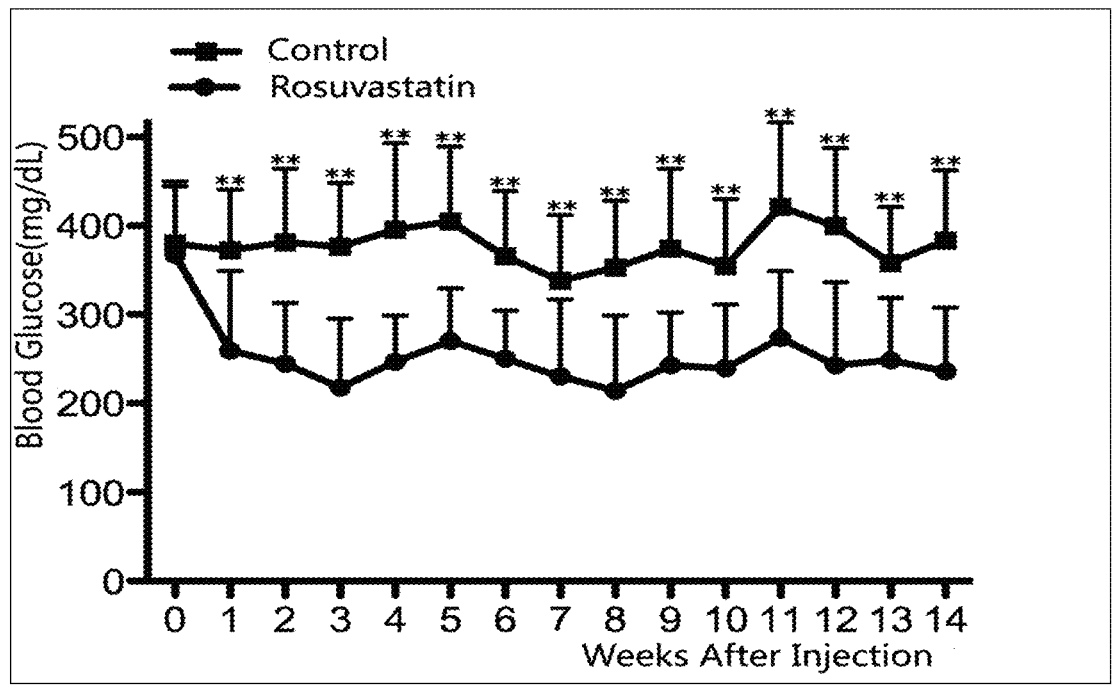
FIG. 11 shows the fasting blood glucose changes 1-14 weeks after a local, single injection of rosuvastatin (see formula of example 5) into femoral marrow cavity in diabetic rats. The fasting blood glucose were detected 1 weeks to 14 weeks after single intraosseous injection of rosuvastatin into the diabetic rats femoral marrow cavity, respectively. At the same time point, blood were collected via rat tail after 12 h of fasting, glucose meter measuring blood glucose changes. The results show that a single local intraosseous injection of rosuvastatin significantly reduced fasting blood glucose, and this effect sustained at least 14 weeks.

The fasting rats blood glucose were detected weekly, 1 weeks after local single intraosseous injection of rosuvastatin by means of femoral medullary cavity. After the rats were fasted 6 h, take one drop of blood (about 50 ul) from the rat tail and placed in the blood sugar test paper (Roche), 2 seconds later, fasting blood glucose were determined by Roche glucose meter (ACCU-CHEK Performa). Results show that blood glucose significantly reduced after a single local intraosseous injection of rosuvastatin by means of femoral medullary cavity, at least continuing to 14 weeks. Results were shown in FIG. 11.

The Experimental Example 11

Glucose Tolerance Test (GTT)

Figure 12:
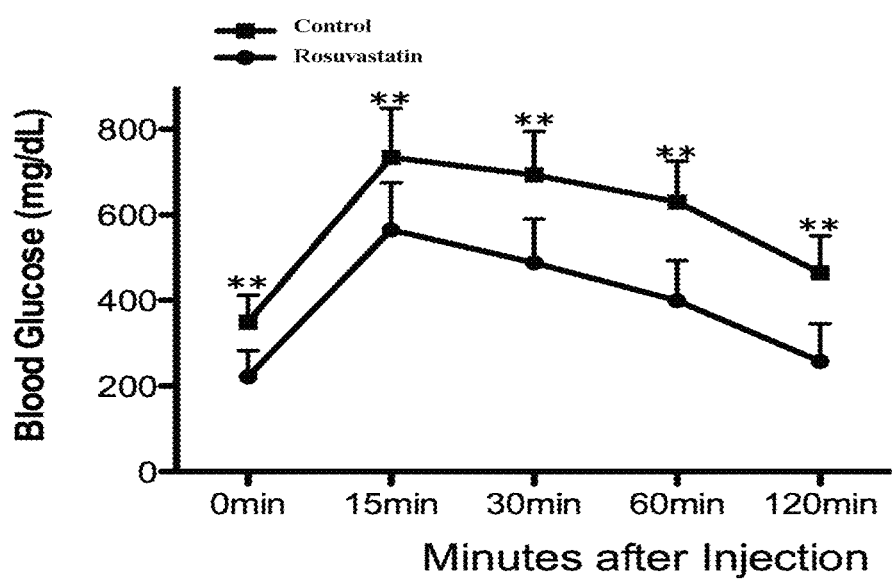
FIG. 12 shows the result of glucose tolerance test (GTT) 11 weeks after a local, single injection of rosuvastatin (see formula of example 5) into femoral marrow cavity in diabetic rats. According to the standard protocol, fasting in rats after 12 h, intraperitoneal injection of glucose (2 g/kg), GTT test were conducted by blood glucose meter.

To further verify anti-diabetic therapeutic effect of single local intraosseous injection of rosuvastatin by means of femoral medullary cavity, we conducted intraperitoneal injection of glucose tolerance tests. 11 weeks after intraosseous injection of rosuvastatin, the rats were overnight fasting for 12 h. After intraperitoneal injection of glucose (2 g/kg, China otsuka pharmaceutical co., LTD), and collecting blood from tail vein 0, 15, 30, 60, 120 minutes respectively, the blood glucose were assayed with blood glucose meter (ACCU-CHEK Performa) blood glucose (Mauvais-Jarvis F, Ueki K, Fruman D A, et al. Reduced expression of the murine p85alpha subunit of phosphoinositide 3-kinase improves insulin signaling and ameliorates diabetes. J Clin Invest. 2002; 109(1): 141-149). Results were shown in FIG. 12.

The Experimental Example 12

A Single Local Intraosseous Injection of Simvastatin by Means of Femoral Medullary Cavity Significantly Decrease Blood Lipid in STZ and High Fat Diet Feeded Rats Intraperitoneal injection of streptozotocin (STZ, Sigma) 40 mg/kg, the second day after the administration, rats were given high-fat diet (purchased from the Institute of Zoology, the formula: Basic materials 68.5%, 20% lard and sucrose 10%, 1% cholesterol, 0.5% porcine bile salts).

The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, simvastatin injection prepared according to Example 1 method, containing simvastatin 5 mg, simvastatin 10 mg or only vehicle (PBS buffer, 0.1% BSA, 2% DMSO) respectively, were injected with micro syringe. Bone wax pinhole puncture closure avoiding leakage and sutured wounds.

Figure 13:
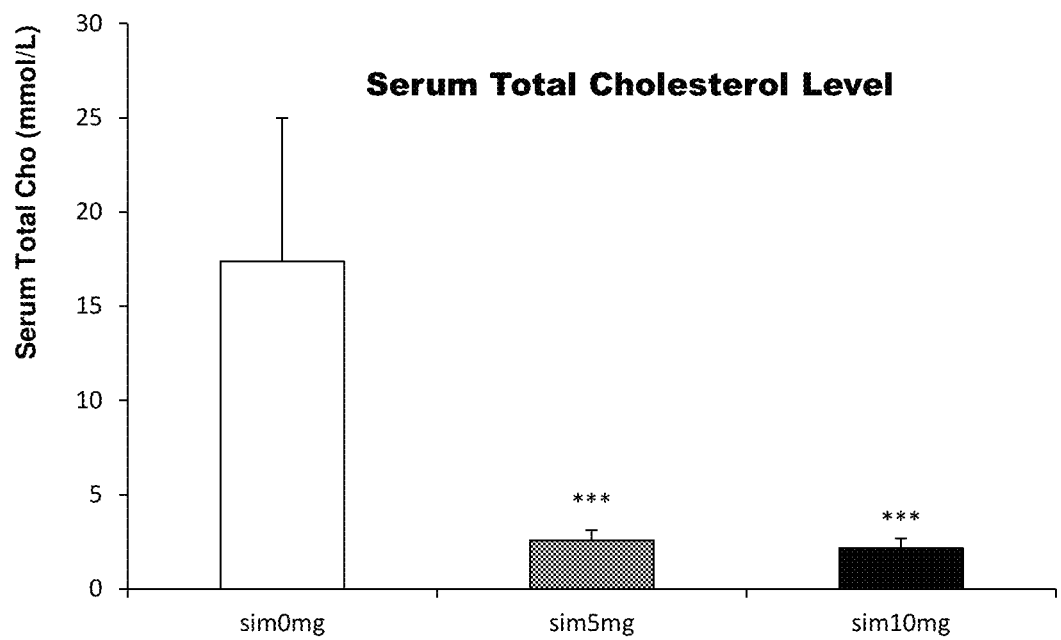
FIG. 13 shows serum cholesterol changes 5 months after a single, local intraosseous injection of simvastatin in the STZ and high-fat diet induced type 2 diabetic rats (compared with the control group, ***$p<0.001$).
Figure 14:
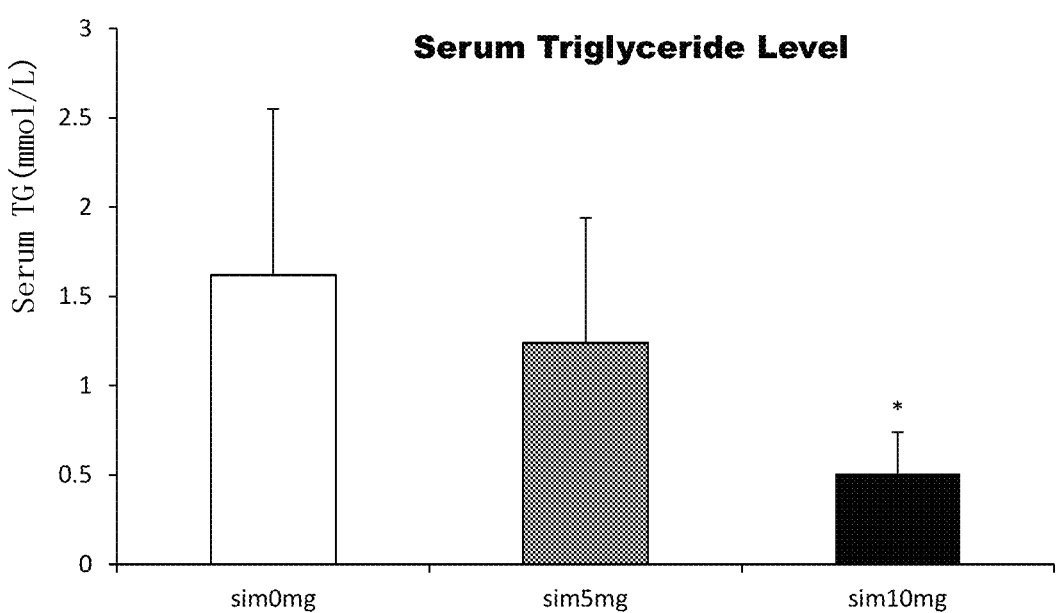
FIG. 14 shows serum triglyceride changes 5 months after a single, local intraosseous injection of simvastatin in the STZ and high-fat diet induced type 2 diabetic rats (compared with the control group, ***$p<0.05$).
Figure 15:
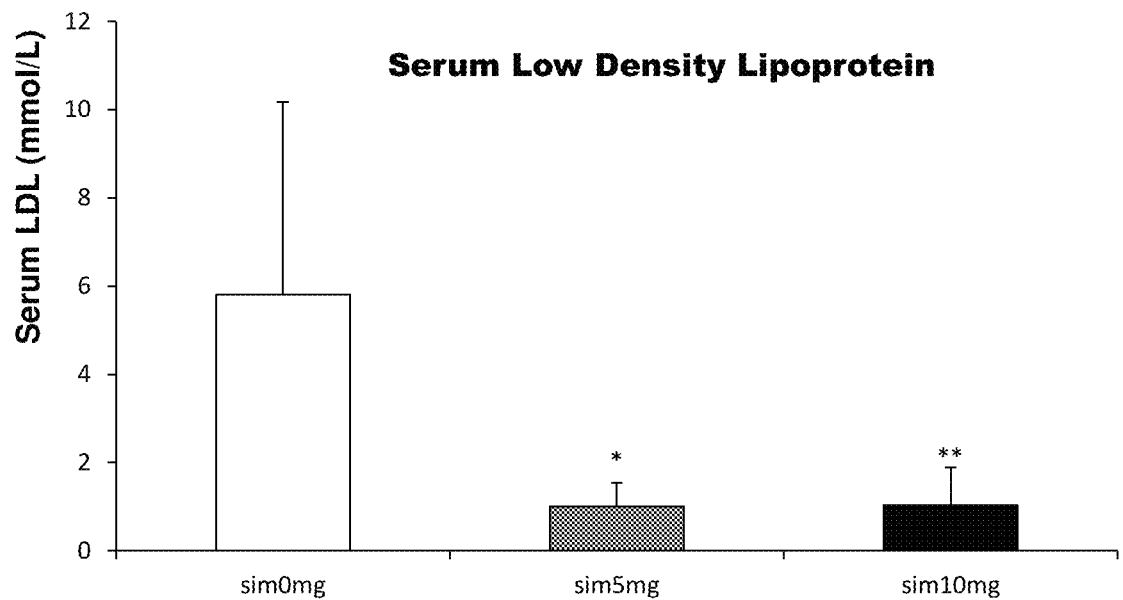
FIG. 15 shows serum low density lipoprotein changes 5 months after a single, local intraosseous injection of simvastatin in the STZ and high-fat diet induced type 2 diabetic rats (compared with the control group, *$p<0.05$, **$p<0.01$).

Five months later, the rats were euthanized by overdose anesthesia, collected the serum, serum cholesterol, triglycerides, low-density lipoprotein were detected. Results show a single intraosseous injection of simvastatin by means of femoral medullary cavity significantly decrease serum cholesterol, triglycerides, LDL even after 5 months (compared with the control group, *<0.05, p<0.01, *p<0.001). Result see FIG. 13 (serum total cholesterol), FIG. 14 (serum triglycerides), FIG. 15 (serum low density lipoprotein).

The Experimental Example 13

A Single Local Intraosseous Injection of Simvastatin by Means of Femoral Medullary Cavity Significantly Increase Liver Function in STZ and High Fat Diet Feeded Rats Intraperitoneal injection of streptozotocin (STZ, Sigma) 40 mg/kg, the second day after the administration, rats were given high-fat diet (purchased from the Institute of Zoology, the formula: Basic materials 68.5%, 20% lard and sucrose 10%, 1% cholesterol, 0.5% porcine bile salts).

The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, simvastatin injection prepared according to Example 1 method, containing simvastatin 5 mg, simvastatin 10 mg or only vehicle (PBS buffer, 0.1% BSA, 2% DMSO) respectively, were injected with micro syringe. Bone wax pinhole puncture closure avoiding leakage and sutured wounds.

Figure 16:
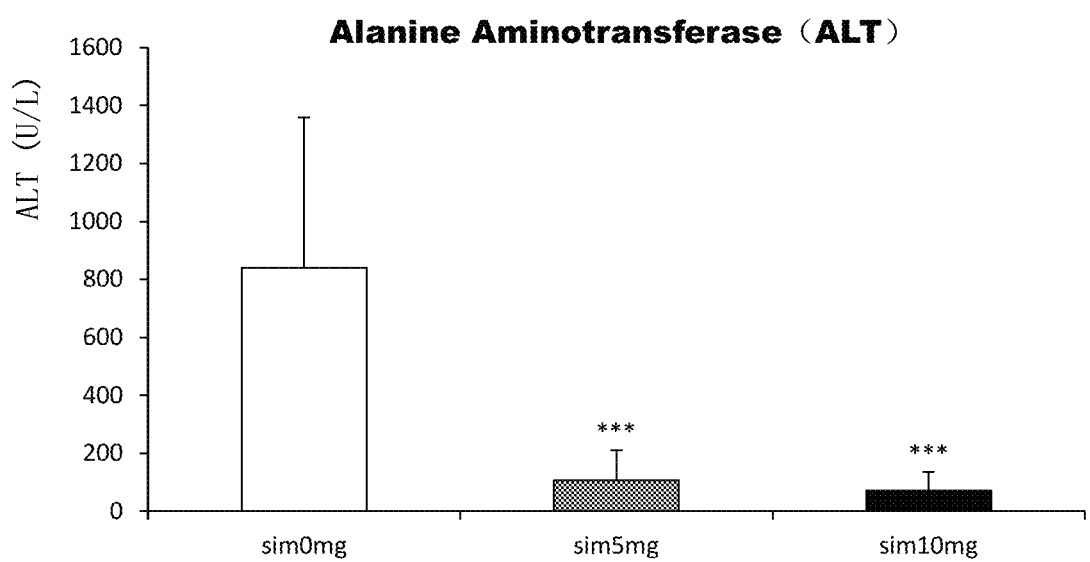
FIG. 16 shows alanine aminotransferase (ALT) changes 5 months after a single, local intraosseous injection of simvastatin in the STZ and high-fat diet induced type 2 diabetic rats (compared with the control group, ***$p<0.001$).
Figure 17:
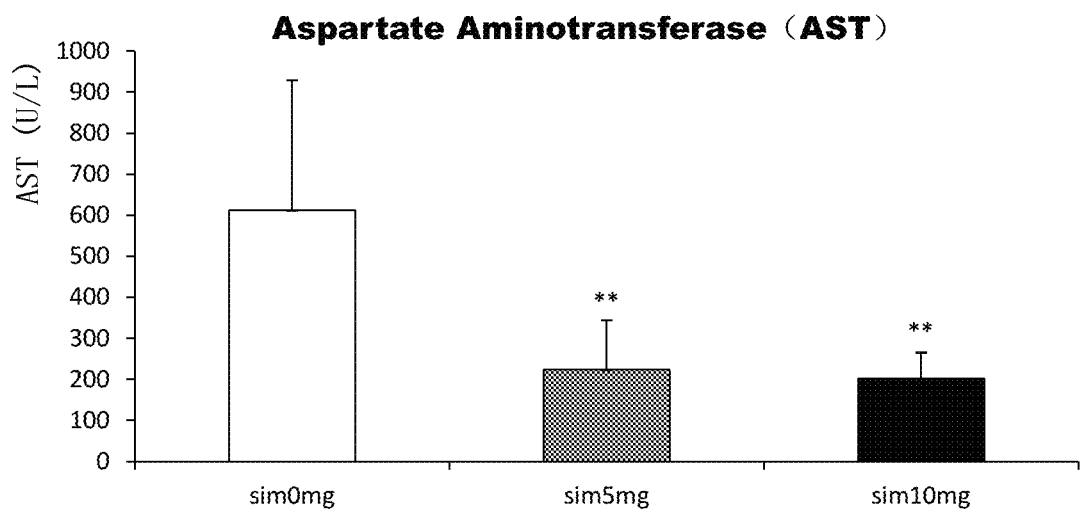
FIG. 17 shows aspartate transaminase (AST) changes 5 months after a single, local intraosseous injection of simvastatin in the STZ and high-fat diet induced type 2 diabetic rats (compared with the control group, **$p<0.01$).

Five months later, the rats were euthanized by overdose anesthesia, collected the serum, alanine aminotransferase (ALT), aspartate aminotransferase (AST) were detected. Results show a single intraosseous injection of simvastatin significantly improved liver function in rats. Results were shown in FIG. 16 (ALT), FIG. 17 (AST).

The Experimental Example 14

A Single Local Intraosseous Injection of Simvastatin by Means of Femoral Medullary Cavity Significantly Reduce Obesity in High Fat Diet Feeded Rats High-fat diet (purchased from the Institute of Zoology, the formula: Basic materials 68.5%, 20% lard and sucrose 10%, 1% cholesterol, 0.5% porcine bile salts) was given to rats. The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, simvastatin injection prepared according to Example 1 method, simvastatin 5 mg, simvastatin 10 mg or only vehicle (PBS buffer, 0.1% BSA, 2% DMSO) respectively, were injected with micro syringe. Bone wax pinhole puncture closure avoiding leakage and sutured wounds.

Figure 18:
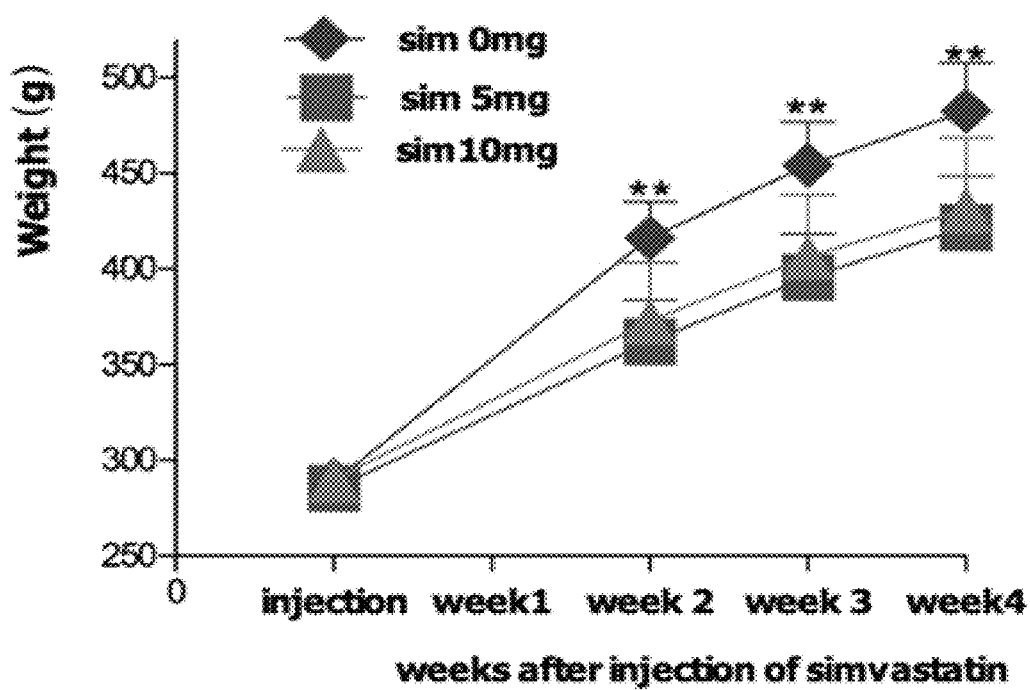
FIG. 18 shows body weight changes 4 weeks after a single, local intraosseous injection of simvastatin in the high-fat diet induced obese rats (compared with the control group, **$p<0.01$).
Figure 19:
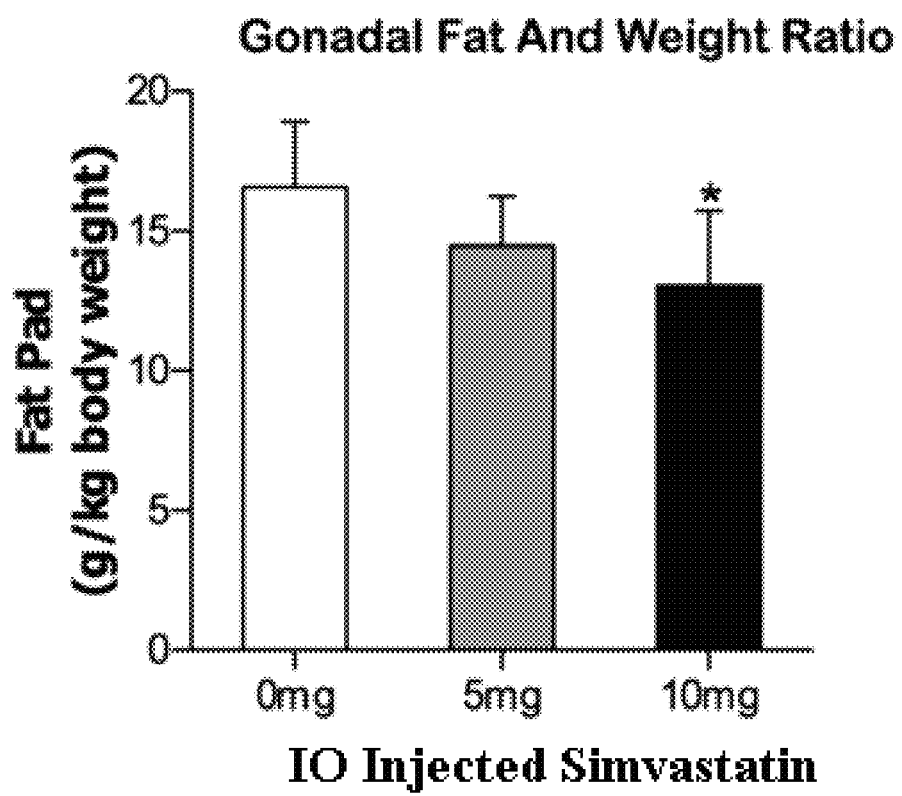
FIG. 19 shows the gonadal fat and body weight ratio 4 weeks after a single, local intraosseous injection of simvastatin in the high-fat diet induced obese rats (compared with the control group, *$p<0.05$).
Figure 20:
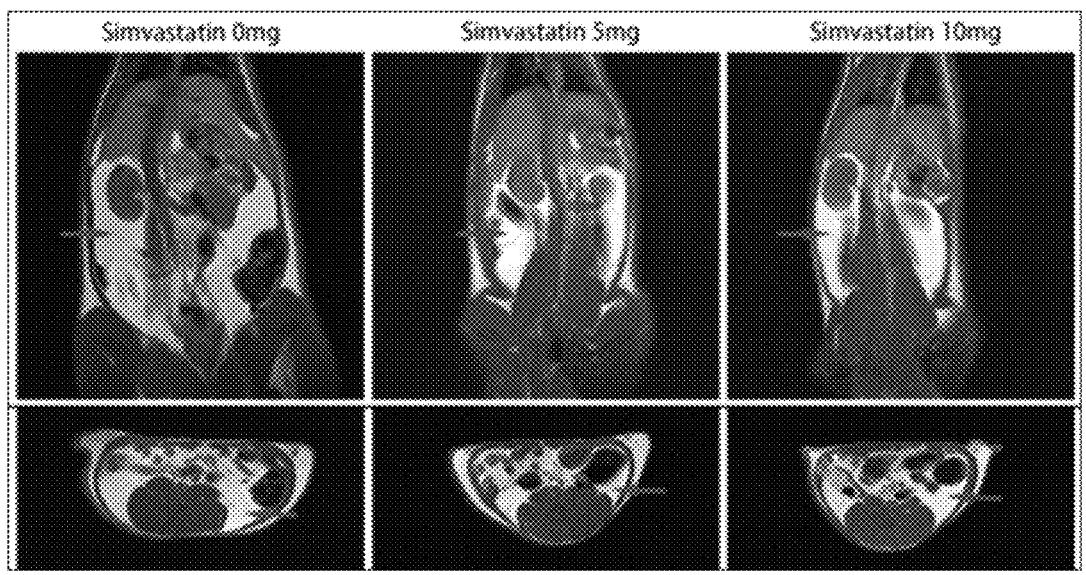
FIG. 20 shows MRI detection of body fat changes 4 weeks after single local intraosseous injections of simvastatin in high-fat diet induced obesity rats. The result shows that in the control group, the rats are obvious obesity, peri-renal fat increase, while in the group with intraosseous injections of simvastatin, the body fat is significantly reduced.

All the rats were weighed once a week after the operation, 4 weeks later, the rats were euthanized by the overdose anesthesia, MRI detection of peri-renal fat, weighing gonadal fat, ratio of gonadal adipose tissue and body weight was calculated. Results showed that a single local intraosseous injection of simvastatin significantly reduced body weight and fat volume. FIG. 18 (body weight), FIG. 19 (ratio of gonadal adipose tissue and body weight), FIG. 20 (MRI detection of peri-renal fat).

The Experimental Example 15

A Single Local Intraosseous Injection of Simvastatin by Means of Femoral Medullary Cavity Significantly Reduce Fat Liver High-fat diet (purchased from the Institute of Zoology, the formula: Basic materials 68.5%, 20% lard and sucrose 10%, 1% cholesterol, 0.5% porcine bile salts) was given to rats. The rats were anesthesiaed by intraperitoneal injection of 10% chloral hydrate anesthesia (3 ml/kg), incised 0.5 cm under the right side of the greater trochanter, in the lateral of femurs, a medullo-puncture needle (diameter 1 mm) penetrate the cortical bone, simvastatin injection prepared according to Example 1 method, containing simvastatin 5 mg, simvastatin 10 mg or only vehicle (PBS buffer, 0.1% BSA, 2% DMSO) respectively, were injected with micro syringe. Bone wax pinhole puncture closure avoiding leakage and sutured wounds.

Figure 21:
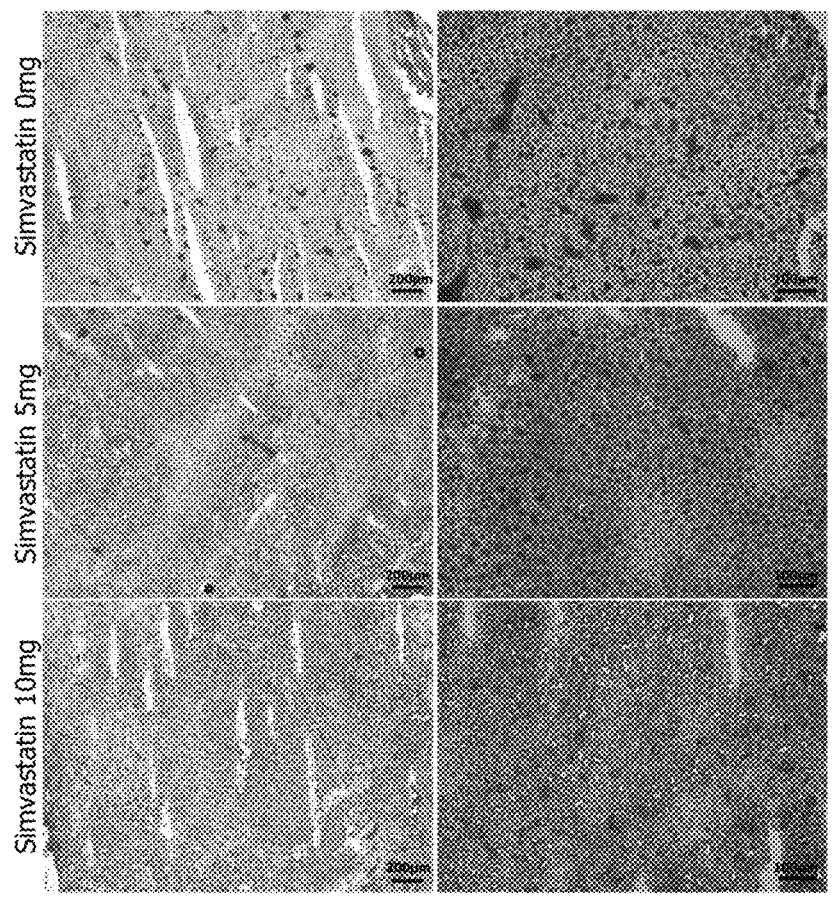
FIG. 21 shows that the fat liver significantly reduced 4 weeks after single local intraosseous injections of simvastatin in high-fat diet induced obese rats.

All the rats were weighed once a week after the operation; the rats were euthanized by the overdose anesthesia 4 weeks later. Rat livers were frozen sectioned and oil red o stain, results show that experimental rats fatty liver were significantly reduced. Results are as shown in FIG. 21.

The Experimental Example 16

A Single Local Intraosseous Injection of Simvastatin by Means of Femoral Medullary Cavity Significantly Reduce Fat Liver High-fat diet (purchased from the Institute of Zoology, the formula: Basic materials 68.5%, 20% lard and sucrose 10%, 1% cholesterol, 0.5% porcine bile salts) was given to rats. The rats were anesthesiaed by intraperitoneal injection of 10% chloral hydrate anesthesia (3 ml/kg), incised 0.5 cm at a sterile environment under the right side of the greater trochanter, in the lateral of femurs, a medullo-puncture needle (diameter 1 mm) penetrate the cortical bone, simvastatin injection prepared according to Example 1 method, containing simvastatin 5 mg, simvastatin 10 mg or only vehicle (PBS buffer, 0.1% BSA, 2% DMSO) respectively, were injected with micro syringe. Bone wax pinhole puncture closure avoiding leakage and sutured wounds.

Figure 22:
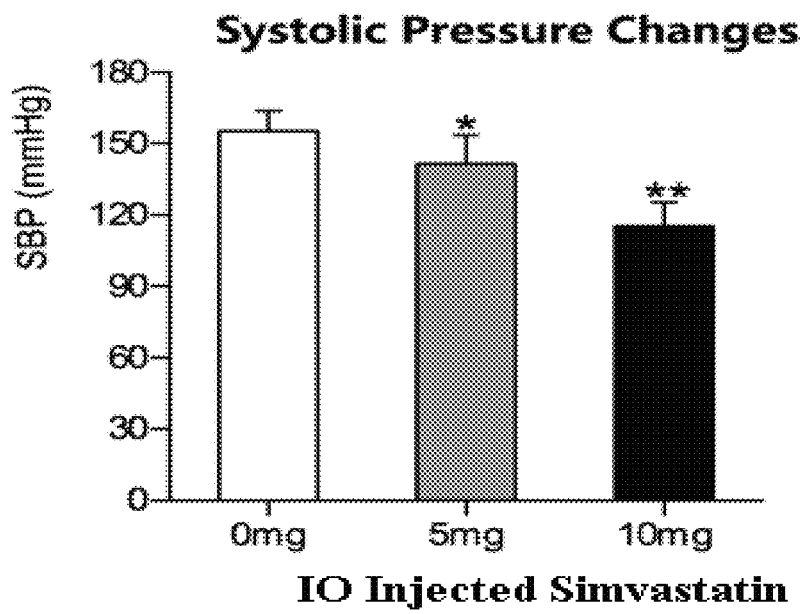
FIG. 22 shows the systolic pressure changes 4 weeks after a single, local intraosseous injection of simvastatin in the high-fat diet induced obese rats (compared with the control group, *$p<0.05$, **$p<0.01$).
Figure 23:
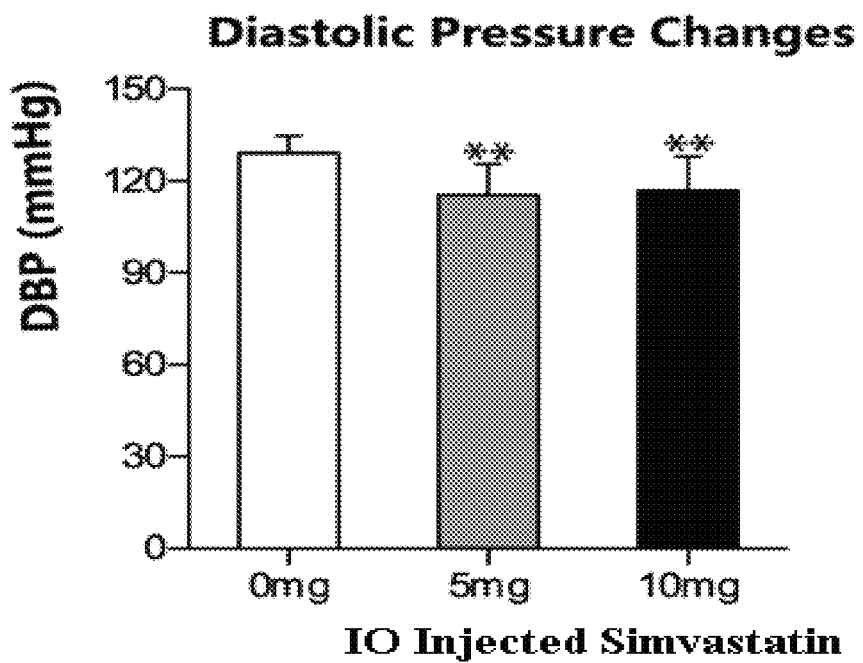
FIG. 23 shows the diastolic pressure changes 4 weeks after a single, local intraosseous injection of simvastatin in the high-fat diet induced obese rats (compared with the control group, **$p<0.01$).
Figure 24:
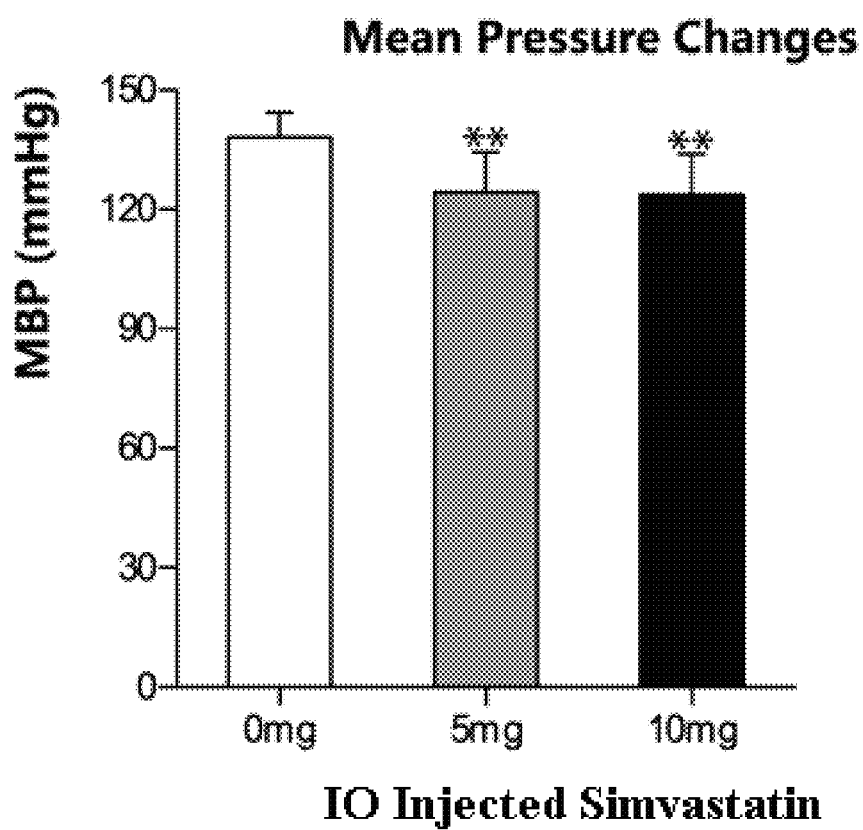
FIG. 24 shows the mean blood pressure changes 4 weeks after a single, local intraosseous injection of simvastatin in the high-fat diet induced obese rats (compared with the control group, **$p<0.01$).

Weigh per week after surgery, rats were anesthetized after 3 weeks and measured blood pressure; results showed that blood pressure was significantly decreased in the experimental group. Results were shown in FIG. 22 (systolic blood pressure), FIG. 23 (diastolic), 24 (mean arterial pressure).

The present invention is not limited to the above embodiments. The above-described embodiments are merely illustrative and not restrictive. Under the inspiration of the present invention, those skilled in the art can make a lot of amendments and modification without departing from the spirit of the present invention, that all fall in the protective scope of the present invention.

The invention claimed is:

1. A pharmaceutical composition for intraosseous treatment of a patient suffering from non-insulin-dependent diabetes, obesity, hypertension, hyperlipidemia, atherosclerosis, cardiovascular disease, cerebrovascular disease, coronary heart disease, stroke, or fatty liver, or for improving fat metabolism in a patient, said pharmaceutical composition comprising:
an intraosseous therapeutically effective amount of a statin compound or its pharmaceutically acceptable salt,
dissolved in phosphate buffered saline (PBS) containing 2% DMSO and 0.1% albumin to form a homogeneous composition,
wherein the concentration of said statin is adapted to provide an intraosseous dosage form for injection of said intraosseous therapeutically effective amount of statin.

2. The pharmaceutical composition of claim 1, wherein said statin is simvastatin.

3. The pharmaceutical composition of claim 1, wherein said albumin is bovine serum albumin (BSA).

* * * * *

UNITED STATES PATENT AND TRADEMARK OFFICE
CERTIFICATE OF CORRECTION

PATENT NO. : 10,632,115 B2
APPLICATION NO. : 15/900103
DATED : April 28, 2020
INVENTOR(S) : Chunli Song et al.

Page 1 of 1

It is certified that error appears in the above-identified patent and that said Letters Patent is hereby corrected as shown below:

On the Title Page

Insert item (30):
--Foreign Application Priority Data
International PCT/CN2013/001429, filed November 22, 2013
Chinese Patent Application No. 20120512630.8, filed November 23, 2012
Chinese Patent Application No. 201310426327.0, filed September 18, 2013.--

Signed and Sealed this
Fourteenth Day of July, 2020

Andrei Iancu
*Director of the United States Patent and Trademark Office*